United States Patent [19]

Yamaguchi et al.

[11] Patent Number: 4,540,818
[45] Date of Patent: Sep. 10, 1985

[54] PROCESS FOR PREPARATION OF 3,3'- OR 3,4'-DIAMINODIPHENYLMETHANE

[75] Inventors: Keizaburo Yamaguchi, Kanagawa; Kenichi Sugimoto, Tokyo; Yoshimitsu Tanabe, Kanagawa; Saburo Kawashima; Akihiro Yamaguchi, both of Kanagawa, all of Japan

[73] Assignee: Mitsui Toatsu Chemicals, Inc., Tokyo, Japan

[21] Appl. No.: 490,730

[22] Filed: May 2, 1983

[30] Foreign Application Priority Data

Mar. 23, 1983 [JP] Japan .................. 58-47097

[51] Int. Cl.³ .............................. C07C 87/50
[52] U.S. Cl. .................... 564/330; 564/329; 564/335; 564/412
[58] Field of Search ............... 564/329, 330, 335, 412

[56] References Cited

U.S. PATENT DOCUMENTS 3,213,139 10/1965 Chase et al. .................. 564/329
3,541,151 11/1970 Coombs et al. ................ 564/329
4,085,141 4/1978 Wedemeyer et al. ........ 564/335 X

OTHER PUBLICATIONS

Montagne, "Berichte", vol. 48, pp. 1027–1037, (1904).
Wagner et al., "Synthetic Organic Chemistry", p. 5 (1963).

*Primary Examiner*—Robert V. Hines
*Attorney, Agent, or Firm*—Albert L. Jeffers; Stephen T. Belsheim

[57] ABSTRACT

Preparation of 3,3'- or 3,4'-diaminodiphenylmethane by catalytically reducing and dechlorinating, in the presence of a reduction catalyst, a dinitrobenzophenone compound having the formula

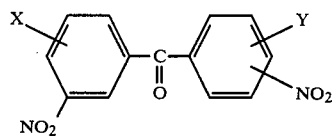

wherein X is chlorine and attached to a position 4 or 6 on the benzene ring, and Y is hydrogen or chlorine with the proviso that when Y is hydrogen, the nitro group is attached to a position 3' or 4', and when Y is chlorine, Y is attached to a position 4' and the nitro group is attached to a position 3'.

9 Claims, No Drawings

PROCESS FOR PREPARATION OF 3,3'- OR 3,4'-DIAMINODIPHENYLMETHANE

BACKGROUND OF THE INVENTION

The present invention relates to a novel process for the preparation of 3,3'- or 3,4'-diaminodiphenylmethane.

3,3'-Diaminodiphenylmethane and 3,4'-diaminodiphenylmethane are useful as monomers for the production of high-molecular compounds, intermediates for the production of agricultural chemicals, pharmacological compounds and dyes, particularly useful as starting materials for the production of polyamides and polyimides having excellent heat resistance.

Herefore, 3,3'-diaminodiphenylmethane has been prepared by condensing 3-nitrobenzyl alcohol with nitrobenzene or condensing nitrobenzene with formaldehyde to prepare 3,3'-dinitrodiphenylmethane which is then reduced in the presence of stannic chloride or iron [L. Gatterman et al., Ber., 27, 2295 (1894); L. Thorp et al., J. Am. Chem. Soc., 37, 373 (1915); M. Schöpff et al., Ber., 27, 2322 (1894)].

3,4'-Diaminodiphenylmethane has been prepared by condensing 4-nitrobenzyl alcohol with nitrobenzene to prepare 3,4'-dinitrodiphenylmethane which is then reduced [L. Gattarmann et al., Ber., 27, 2293 (1894)].

However, even when the condensation reaction between benzyl alcohol and nitrobenzene or between nitrobenzene and formalin is conducted for a long period of time by using a large amount of concentrated sulfuric acid, these processes result in yields of dinitrodiphenylmethane of as low as only 20 to 30%. Further, dinitrodiphenylmethane must be reduced in the presence of a tin compound or iron to obtain diaminodiphenylmethane. But, it is bothersome to separate the metallic compound used for the reduction from the product and it is necessary to pay attention lest trace amounts of the metal should remain in the product.

Thus the conventional processes of preparing dinitrodiphenylmethane by the known condensation reaction and reducing it to prepare diaminodiphenylmethane have disadvantages in that they require much cost and effort for the disposal of a large amount of various waste materials to prevent them from causing environmental pollution or for the recovery of them, and in addition thereto the desired product is obtained in a low yield. Accordingly, these processes are industrially unfavorable from the viewpoints of economy and environmental protection.

SUMMARY OF THE INVENTION

An object of the present invention is to provide an industrially advantageous and economical process for the preparation of 3,3'- or 3,4'-diaminodiphenylmethane.

Another object of the present invention is to provide a process for the preparation of 3,3'- or 3,4'-diaminodiphenylmethane in a high yield.

Still another object of the present invention is to provide a process which does not require much cost and effort as compared with the conventional processes for the disposal of a large amount of various waste materials, formed as by-products in manufacturing processes, to prevent them from causing environmental pollution and which is excellent in the viewpoint of environmental protection.

In accordance with this invention, it is possible to prepare 3,3'- or 3,4'-diaminodiphenylmethane by catalytically reducing and dechlorinating, in the presence of a reduction catalyst, a dinitrobenzophenone having the formula

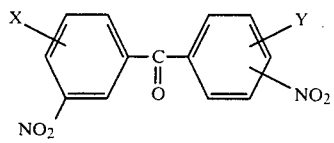

wherein X is chlorine and attached to a position 4 or 6 on the benzene ring, Y is hydrogen or chlorine with the proviso that when Y is hydrogen, the nitro group is attached to a position 3' or 4', and when Y is chlorine, Y is attached to a position 4' and the nitro group is attached to a position 3'.

The process of the present invention has advantages in that it does not require much cost and effort for the disposal of a large amount of various waste materials to prevent them from causing environmental pollution or for the recovery of them and in addition thereto the desired product can be prepared in a high yield, while the conventional processes of preparing 3,3'- or 3,4'-dinitrodiphenylmethane by the known condensation reaction and reducing it require much cost and effort.

The process of the present invention comprising dechlorinating a dinitrochlorobenzophenone compound as reducing its nitro groups and further converting its carbonyl group into a methylene group is not known by those skilled in the art. Therefore, the present invention provides a novel process for the preparation of 3,3'- or 3,4'-diaminodiphenylmethane which can be prepared industrially advantageously.

DETAILED DESCRIPTION OF THE INVENTION

The present invention relates to a process for the preparation of 3,3'- or 3,4'-diaminodiphenylmethane by catalytically reducing and dechlorinating, in the presence of a reduction catalyst, the dinitrobenzophenone compound represented by the above formula to obtain 3,3'- or 3,4'-diaminodiphenylmethane hydrochloride followed by neutralization with ammonia or an amine.

Typical dinitrobenzophenones that can be used as starting materials in the practice of the present invention include 3,3'-dinitro-4,4'-dichlorobenzophenone, 3,3'-dinitro-6,4'-dichlorobenzophenone, 3,3'-dinitro-6-chlorobenzophenone, 3,3'-dinitro-4-chlorobenzophenone, 3,4'-dinitro-6-chlorobenzophenone and 3,4'-dinitro-4-chlorobenzophenone.

These dinitrobenzophenones can be easily obtained by nitrating the corresponding halogenobenzophenones such as 4,4'-dichlorobenzophenone, 4-chlorobenzophenone, 4-nitro-6'-chlorobenzophenone, 4-chloro-4'-nitrobenzophenone and 2,4'-dichlorobenzophenone.

For example, 3,3'-dinitro-4,4'-dichlorobenzophenone can be prepared in a yield of 95 to 98% by nitrating 4,4'-dichlorobenzophenone [E. R. Kofanov et al., J. Org. Chem. USSR, 15, 98–100 (1979)]. 5,3'-Dinitro-2,4'-dichlorobenzophenone can be prepared in a high yield by nitrating 2,4'-dichlorobenzophenone [E. H. Faith et al., J. Am. Chem. Soc., 77, 543 (1955)]. 3,3'-Dinitro-4-chlorobenzophenone can be prepared in a high yield by nitrating 4-chlorobenzophenone [G. S. Mironov et al., J. Org. Chem. USSR, 8, 1538 (1972)]. 3,4'-Dinitro-4- chlorobenzophenone can be prepared by nitrating 4-halogeno-4'-nitrobenzophenone obtained by the condensation reaction between p-nitrobenzoyl chloride and chlorobenzene [P. T. Montagne et al., Ber., 49, 2267–2270 (1916); G. S. Mironov et al., J. Org. Chem. USSR, 8, 1538–1543 (1972)]. 3,3'-Dinitro-6,4'-dichlorobenzophenone can be prepared in a high yield by nitrating 2,4'-dichlorobenzophenone obtained by the condensation reaction between 2-chlorobenzoyl chloride and chlorobenzene [H. F. Faith et al., J. Am. Chem. Soc., 77, 543 (1955)].

As reduction catalysts suitable for use in the practice of the present invention, metal catalysts which are conventionally used in catalytic reduction may be used. Examples of the metals are nickel, palladium, platinum, rhodium, ruthenium, cobalt and iron. Palladium catalyst is industrially preferred. These catalysts may be used in a metallic form, but they are generally supported on a carrier such as carbon, barium sulfate, silica gel or alumina. Nickel, cobalt and copper may be used in the form of a Raney catalyst.

The catalyst is used in an amount of from 0.05 to 10% by weight based on that of the starting dinitrobenzophenone. When the catalyst is used in a metallic form, the amount is usually within the range of from 2 to 10% by weight. When supported on a carrier, the amount is within the range of from 0.1 to 5% by weight.

Generally, the reaction of the present invention is conducted in an organic solvent. Any of organic solvents which are inert to the reaction of the present invention may be used without particular limitation. Examples of such organic solvents include alcohols such as methanol, ethanol and isopropyl alcohol; glycols such as ethylene glycol and propylene glycol; ethers such as ether, dioxane, tetrahydrofuran and methyl cellosolve; aliphatic hydrocarbons such as hexane and cyclohexane; aromatic hydrocarbons such as benzene, toluene and xylene; esters such as ethyl acetate and butyl acetate; halogenated hydrocarbons such as dichloromethane, chloroform, carbon tetrachloride, 1,2-dichloroethane, 1,1,2-trichloroethane and tetrachloroethane; N,N-dimethylformamide and dimethyl sulfoxide. Hydrogen chloride or hydrochloric acid in a molar ratio of 1 to 2 may be previously added to these solvents to carry out the reduction of the present invention. When an organic solvent immiscible with water is employed and the reaction proceeds too slow, the reaction can be accelerated by adding a conventional phase transfer catalyst such as a quaternary ammonium salt or a quaternary phosphonium salt. The solvent is used in an amount sufficient to suspend the starting dinitrobenzophenones or to completely dissolve them. There is no particular upper limit for the amount of the solvent to be used, but the solvent is usually used in an amount of 0.5 to 10 times by weight that of the starting material.

The reaction temperature is usually within the range of from 20° to 200° C., preferably 50° to 150° C.

The reaction pressure is usually within the range of from atmospheric pressure to 50 kg/cm²G.

In the practice of the present invention, the dinitrobenzophenone compound is suspended or dissolved in a solvent and a reduction catalyst is added thereto. Hydrogen is introduced into the mixture with stirring at a predetermined temperature to convert the nitro groups into amino groups and the carbonyl group into a methylene group and to effect dechlorination, thus obtaining 3,3'- or 3,4'-diaminodiphenylmethane hydrochloride.

The reaction mixture is filtered to recover a mixture composed of the desired hydrochloride and the catalyst. Then the mixture is dissolved in a 70–90% aqueous isopropyl alcohol solution with heating, and filtered. The filtrate is cooled to precipitate pure 3,3'- or 3,4'-diaminodiphenylmethane hydrochloride which is then isolated by filtration. The isolated hydrochloride is dissolved in water and then neutralized to give free 3,3'- or 3,4'-diaminodiphenylmethane.

The progress of the reaction can be traced by the absorption of a theoretical amount of hydrogen or by means of thin-layer chromatography.

The following examples further illustrate the present invention in more detail.

EXAMPLE 1

34.1 g (0.1 mol) of 3,3'-dinitro-4,4'-dichlorobenzophenone, 3.4 g of 5% Pd/C catalyst (a product of Nippon Engelhardt K.K.) and 100 ml of dioxane were charged in a closed glass vessel equipped with a thermometer and a stirrer. While stirring the mixture at a temperature of 80° to 85° C., hydrogen was introduced thereinto and 21.8 l (0.97 mol) of hydrogen was absorbed in 10 hours. Since no more absorption of hydrogen was observed, the reaction was terminated at this point.

The reaction mixture was cooled to room temperature. A precipitate was recovered by filtration and washed with 10 ml of dioxane to obtain a black filter cake. This filter cake was dissolved in 100 ml of an 80% aqueous isopropyl alcohol solution with heating. The solution was filtered with heating to remove the catalyst. The filtrate was cooled to precipitate 3,3'-diaminodiphenylmethane dihydrochloride as a white needle crystal. This product was recovered by filtration, washed with 10 ml of a 90% aqueous isopropyl alcohol solution, and dried to give 20.3 g (yield 75%) of pure 3,3'-diaminodiphenylmethane dihydrochloride as a white needle crystal with m.p. above 260° C.

Elementary analysis for $C_{13}H_{16}N_2Cl_2$: Calculated (%): C 57.6, H 6.0, N 10.3, Cl 26.1. Found (%): C 57.4, H 6.1, N 10.3, Cl 25.9.

EXAMPLE 2

34.1 g (0.1 mol) of 3,3'-dinitro-4,4'-dichlorbenzophenone, 1.5 g of 5% Pd/C, and 100 ml of ethanol were charged in a closed glass vessel equipped with a thermometer and a stirrer. While stirring the mixture at a temperature of 50° to 60° C., hydrogen was introduced thereinto and 22.9 l (1.02 mol) of hydrogen was absorbed in 7.5 hours. Since no more absorption of hydrogen was observed, the reaction was terminated at this point. The reaction solution was neutralized with 13.4 g (0.22 mol) of 28% aqueous ammonia and filtered to remove the catalyst. The filtrate was concentrated to give 3,3'-diaminodiphenylmethane as a brown oil. A high performance liquid chromatography revealed that the purity was 93.8%.

This brown oil was vacuum-distilled to give 16.8 g (yield 85%) of a fraction having a boiling point of 228° to 229° C./5 mmHg. The purity was 99.9%.

This fraction was recrystallized from benzene to give a pure product as a white prismatic crystal with m.p. of 84.5° to 85° C.

Elementary analysis for $C_{13}H_{14}N_2$: Calculated (%): C 78.7, H 7.1, N 14.1. Found (%): C 78.7, H 7.2, N 14.1.

EXAMPLE 3

34.1 g (0.1 mol) of 3,3'-dinitro-6,4'-dichlorobenzophenone, 1 g of palladium black catalyst and 100 ml of ethyl cellosolve were charged in a closed glass vessel equipped with a thermometer and a stirrer. While stirring the mixture at a temperature of 75° to 80° C., hydrogen was introduced thereinto and 22.3 l (1.0 mol) of hydrogen was absorbed in 5 hours. Since no more absorption of hydrogen was observed, the reaction was terminated at this point. The reaction solution was neutralized with 42 g (0.21 mol) of a 20% aqueous caustic soda solution and filtered to remove the catalyst. The filtrate was concentrated and vacuum-distilled to give 15.6 g (yield 78.7%) of a fraction having a boiling point of 228° to 229° C./5 mmHg.

Purity: above 99.9%.

EXAMPLE 4

15.3 g (0.05 mol) of 3,3'-dinitro-4-chlorobenzophenone, 1.5 g of 10% Pt/C and 50 ml of diethylene glycol dimethyl ether were charged in an autoclave. While stirring the mixture at a temperature of 100° to 110° C., hydrogen was introduced. The reaction was conducted for two hours while keeping the pressure at 10 Kg/cm²G. After the completion of the reaction, the reaction mixture was cooled and neutralized with 3.7 g (0.06 mol) of 28% aqueous ammonia. The catalyst was removed by filtration. The filtrate was concentrated and vacuum-distilled to give 7.9 g (yield 79.8%) of a fraction having a boiling point of 228° to 229° C./5 mmHg.

EXAMPLE 5

30.7 g (0.1 mol) of 3,3'-dinitro-4-chlorobenzophenone, 1.5 g of 5% Pd/C and 100 ml of ethanol were charged in a closed glass vessel equipped with a thermometer and a stirrer. While stirring the mixture at a temperature of 65° to 70° C., hydrogen was introduced thereto and 20.1 l (0.9 mol) of hydrogen was absorbed in 6 hours. Since no more absorption of hydrogen was observed, the reaction was terminated at this point. The reaction mixture was cooled to room temperature and filtered to obtain a black filter cake. This filter cake was dissolved in 100 ml of a 90% aqueous isopropyl alcohol solution with heating. The catalyst was removed by filtration with heating. The filtrate was cooled to precipitate 3,3'-diaminodiphenylmethane hydrochloride as a crystal. This crystal was recovered by filtration, washed with 10 ml of isopropanol and neutralized with dilute aqueous ammonia to precipitate a white crystal. The crystal was recovered by filtration and dried in vacuo to give 16.3 g (yield 82.2%) of 3,3'-diaminodiphenylmethane.

EXAMPLES 6 TO 9

The experiment of Example 2 was repeated except that the catalysts, the solvents, the reaction temperatures and the pressures given in Table 1 were employed to give the desired product.

TABLE 1

| Example No. | Catalyst (g) | Solvent (ml) | Reaction temp./time (°C./hr) | Reaction pressure (kg/cm².G) | Yield (%) |
|---|---|---|---|---|---|
| 6 | Raney nickel 3.5 | ethylene glycol | 100–110/5 | 2–3 | 72 |
| 7 | Palladium black 1 | 150 ethyl acetate | 70–75/12 | atmospheric pressure | 77 |
| 8 | 10% Pt/C 7 | ethanol 100 | 70–75/10 | atmospheric pressure | 71 |
| 9 | 5% Pd/C 5 | benzene 100 | 70–75/28 | 10–11 | 62 |

EXAMPLE 10

15.3 g (0.05 mol) of 3,4'-dinitro-4-chlorobenzophenone, 0.75 g of 5% Pd/C and 50 ml of ethyl cellosolve were charged in a closed glass vessel equipped with a thermometer and a stirrer. While stirring the mixture at a temperature of 75° to 80° C., hydrogen was introduced thereinto and 10.3 l (0.46 mol) of hydrogen was absorbed in 13 hours. Since no more absorption of hydrogen was observed, the reaction was terminated at this point. The reaction solution was neutralized with 3.6 g (0.06 mol) of 28% aqueous ammonia. The catalyst was removed by filtration. The filtrate was concentrated to obtain 3,4'-diaminodiphenylmethane as a brown oil. A high performance liquid chromatography revealed that the purity was 88.2%.

This brown oil was vacuum-distilled to give 7.9 g (yield 79.7%) of 3,4'-diaminodiphenylmethane having a purity of 99.7% according to a high performance liquid chromatography.

This product was recrystallized from water to give a pure product as a white needle crystal with m.p. of 85° to 87° C.

Elementary analysis for $C_{13}H_{14}N_2$: Calculated (%): C 78.7, H 7.1, N 14.1. Found (%): C 78.5, H 7.1, N 14.0.

EXAMPLE 11

The reduction of 15.3 g (0.05 mol) of 3,4'-dinitro-4-chlorobenzophenone was conducted in a similar manner to that of Example 10. After the completion of the reaction, the catalyst was immediately removed by filtration with heating. 5.2 g (0.05 mol) of concentrated hydrochloric acid was added to the filtrate. Upon cooling, a light brown needle crystal was precipitated. The crystal was recovered by filtration, washed with isopropanol, and dried to give 8.9 g (yield 66%) of 3,4'-diaminodiphenylmethane hydrochloride. This crude crystal was recrystallized from aqueous isoprpanol solution to give pure 3,4'-diaminodiphenylmethane hydrochloride as a white crystal with m.p. above 210° C. (slowly decomposed).

Elementary analysis for $C_{13}H_{16}N_2Cl_2$: Calculated (%): C 57.6, H 6.0, N 10.3, Cl 26.1. Found (%): C 57.3, H 6.2, N 10.2, Cl 25.9.

What is claimed is:

1. A process for the preparation of 3,3'- or 3,4'-diaminodiphenylmethane, which comprises catalytically reducing and dechlorinating, in the presence of a reduction catalyst, a dinitrobenzophenone compound having the formula

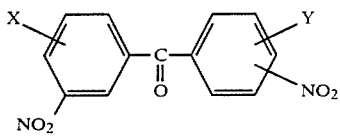

wherein X is chlorine and attached to a position 4 or 6 on the benzene ring, and Y is hydrogen or chlorine with the proviso that when Y is hydrogen, the nitro group is attached to a position 3' or 4', and when Y is chlorine, Y is attached to a position 4' and the nitro group is attached to a position 3'.

2. A process as set forth in claim 1, wherein the reduction catalyst is a metal catalyst for use in catalytic reduction.

3. A process as set forth in claim 1, wherein the catalyst is used in an amount of 0.05 to 10% by weight based on the amount of the dinitrobenzophenone compound.

4. A process as set forth in claim 1, wherein the reaction temperature is within the range of 20° to 200° C.

5. A process as set forth in claim 1, wherein the reaction is conducted in an organic solvent.

6. A process as set forth in claim 2, wherein the metal catalyst is nickel, palladium, platinum, rhodium, ruthenium or cobalt.

7. A process as set forth in claim 6, wherein the metal catalyst is supported on a catalyst carrier.

8. A process as set forth in claim 6, wherein the metal catalyst is a Raney catalyst.

9. A process as set forth in claim 5, wherein the organic solvent is selected from the group consisting of alcohols, glycols, ethers, aliphatic hydrocarbons, aromatic hydrocarbons, halogenated hydrocarbons, N,N-dimethylformamide and dimethyl sulfoxide.

* * * * *